(12) United States Patent
Karl et al.

(10) Patent No.: US 9,968,789 B2
(45) Date of Patent: May 15, 2018

(54) TEMPORARY EXTERNAL PACEMAKER AND MONITOR

(71) Applicants: Mitchell Karl, Boca Raton, FL (US); Martin Kloosterman, Boca Raton, FL (US); Arthur H. Katz, Palm Beach Gardens, FL (US); Marc Schonberger, Weston, FL (US); Daniel Weiss, Boca Raton, FL (US)

(72) Inventors: Mitchell Karl, Boca Raton, FL (US); Martin Kloosterman, Boca Raton, FL (US); Arthur H. Katz, Palm Beach Gardens, FL (US); Marc Schonberger, Weston, FL (US); Daniel Weiss, Boca Raton, FL (US)

( * ) Notice: Subject to any disclaimer, the term of this patent is extended or adjusted under 35 U.S.C. 154(b) by 76 days.

(21) Appl. No.: 14/862,211

(22) Filed: Sep. 23, 2015

(65) Prior Publication Data

US 2017/0080236 A1 Mar. 23, 2017

(51) Int. Cl.
| | |
|---|---|
| *A61N 1/362* | (2006.01) |
| *A61N 1/365* | (2006.01) |
| *A61B 5/00* | (2006.01) |
| *A61B 5/0245* | (2006.01) |
| *A61B 5/04* | (2006.01) |
| *A61B 5/0464* | (2006.01) |

(Continued)

(52) U.S. Cl.
CPC ........ *A61N 1/36585* (2013.01); *A61B 5/0002* (2013.01); *A61B 5/0245* (2013.01); *A61B 5/04018* (2013.01); *A61B 5/0464* (2013.01); *A61B 5/0472* (2013.01); *A61B 5/053* (2013.01); *A61B 5/6823* (2013.01); *A61B 5/6831* (2013.01); *A61B 5/7405* (2013.01); *A61B 5/746* (2013.01); *A61N 1/3625* (2013.01); *A61N 1/36521* (2013.01)

(58) Field of Classification Search
CPC ..... A61N 1/046; A61N 1/0484; A61N 1/3625
See application file for complete search history.

(56) References Cited

U.S. PATENT DOCUMENTS 5,078,134 A * 1/1992 Heilman .............. A61B 5/6831
600/508
6,148,233 A * 11/2000 Owen .................. A61N 1/0452
607/5

(Continued)

*Primary Examiner* — George Evanisko
(74) *Attorney, Agent, or Firm* — Johnson & Martin, P.A.; James David Johnson

(57) ABSTRACT

A device for ambulatory monitoring for suspected bradycardia or QT monitoring with simultaneous external pacing capability is provided. The device monitors the patient for a significant bradycardic episode and/or prolongation of the QT interval. The device provides a monitor having sensing, pacing, recording and transmission capabilities. At least two pacing electrodes are provided with adhesive backing for application to the anterior chest region with one cathode to the region of the cardiac apex and an anode to the region of the right upper sternal cardiac border. If a bradycardic episode is detected or prolongation of the QT is sufficient, then pacemaking energy is provided to the electrodes allowing the patient time to seek medical care without suffering the results of temporary hemodynamic instability that might otherwise be associated with dysrhythmia.

17 Claims, 3 Drawing Sheets

(51) Int. Cl.
   *A61B 5/0472*  (2006.01)
   *A61B 5/053*   (2006.01)

(56) References Cited

U.S. PATENT DOCUMENTS

| | | | |
|---|---|---|---|
| 2010/0305633 A1* | 12/2010 | Aziz | A61N 1/39 607/3 |
| 2016/0158527 A1* | 6/2016 | Jensen | A61N 1/08 607/142 |
| 2016/0271384 A1* | 9/2016 | Kaib | A61N 1/046 |

* cited by examiner

TEMPORARY EXTERNAL PACEMAKER AND MONITOR

FIELD OF THE INVENTION

The invention relates to a bradycardia and QT interval monitor and pacemaker. More particularly, the invention relates to an ambulatory, external bradycardia and QT interval monitor and pacemaker that provides real-time sensing, pacing, recording, and transmitting capabilities.

BACKGROUND

Cardiac monitoring is often recommended for patients with palpitations, those with syncope, and those whose medication changes or whose electrocardiogram indicates dysrhythmia. Tachyarrhythmias are most often treated with medications, however, one prominent side effect of their usage is the possibility of induction of bradycardia. Another possible side effect that can result from the use of these medications is prolongation of the QT interval, which can lead to torsade de pointes and which may be life-threatening. Short-term monitoring often takes the form of hospitalization and telemetry observation, or alternatively, outpatient monitoring for 24 hours or longer periods such as might be feasible with a loop recorder.

The physician is often forced to make a judgment as to the likelihood of a symptomatic bradycardia requiring pacing on a temporary basis. If home monitoring is selected, any significant, symptomatic bradycardia is recorded but not treated, and therefore, a bradycardic episode possibly may be documented without the ability to administer timely therapy.

Selection of hospitalization for observation allows fast treatment of an identified bradycardia or in the case of prolonged QT interval, torsade de pointes. Such treatment may include withdrawal of any offending agent, in the case of bradycardia treatment with atropine, and in the case of either bradycardia or torsade, temporary external or internal pacing. To err on the side of hospitalization drives up cost and inconvenience for a large number of patients with the actual bradycardia therapy or therapy for torsade being administered to relatively few. To err on the side of outpatient monitoring without the ability to treat a recorded bradyarrhythmia or torsade risks the life of the patient. Further, even longer term monitoring for suspected dysrhythmias such as transtelephonic monitoring systems or the Medtronic Reveal system or newer injectable loop recorders risks the bradycardic rhythm not being treated in a timely fashion sufficient to prevent patient injury.

Many situations such as bundle branch block, prolonged, symptomatic HV, fractionated His bundles, tachy-brady, Wenckebach heart block, and medication initiation or escalation raise suspicion for bradycardia or torsade that may require pacing. The decision of whether to pace a patient is often a judgment call because only after a symptomatic bradycardic event is revealed is the patient a definite pacemaker candidate. Unfortunately, once a sufficient event has occurred the patient may have already been injured. However, to offer a pacemaker before sufficient event increases the cost, patient doubt, and physician scrutiny.

Current bradycardia management is typically divided into a diagnostic arm and a therapeutic arm. The implications are that only after the bradycardia has been determined on a monitor is the patient a candidate for permanent pacing. Indications for permanent pacing are in a constant revision to balance between preventing too many pacemaker implantations in those who do not need them, but to allow those with sufficient evidence to suggest that they may need one to obtain one prior to a catastrophic event. These indications are based on statistic likelihoods of symptomatic bradycardic rhythms, but are not sufficiently patient specific or predictive to ensure that the correct decision is made. Thus, some patients receive pacemakers, but never truly require them, while other patients do not technically qualify for a pacemaker under current indications, but subsequently have an event that was suspected but was not treated by pacing at the time it occurred.

Although external pacing systems exist, their usage has been exclusively to treat bradycardia in hospitalized patients. An external pacing system for outpatient use is not known to exist.

What is needed is a device that is not cumbersomely large and that can sense bradycardia, treat in real time with external pacing, record the dysrhythmia, and transmit it to a health care professional. A further need exists for a device that can sense prolongation of the QT interval in patients that are subject to initiation or escalation of antiarrhythmic therapy and deliver pacing to overdrive suppressed potential torsade de pointes, and therefore, prevent injury or death in those patients as well.

SUMMARY

The present invention provides a device for ambulatory monitoring for suspected bradycardia with simultaneous external pacing capability, recording capability, and transmitting capability. The device is also able to detect prolongation of the QT interval and deliver pacing at a rate sufficient to shorten the QT interval and decrease the likelihood of sustained torsade, which may be potentially life-threatening. This therapy allows the patient time to present himself or herself to a physician or health care facility without suffering the result of temporary hemodynamic instability that might otherwise be associated with a bradycardia or torsade. After the dysrhythmia has occurred, if it is a bradycardia, a permanent pacemaker may be offered based on the documented bradycardia in an otherwise stable patient. In this way the invention acts as a bridge between the diagnosis and more definitive therapy for patients with bradycardia. The diagnosis and recommendations for pacemakers is greatly improved using this present invention. In properly selected patients, use of the device may also allow the avoidance of hospitalization entirely in those that have initiation or escalation of antiarrhythmic therapy with risk of torsade from prolongation of the QT interval.

Specifically, the present invention provides a monitor having sensing, pacing, recording, and transmitting capabilities. The pacing current delivery involves pulsations of approximately 40 (Zoll) or 20 (all others) millisecond pulses with the capability of delivering up to 140-200 milliamps. This device uses a battery, which in preferred embodiments can be a rechargeable lithium battery, with a low battery indicator light and a periodic beep tone at critically low battery levels. At least two pacing electrodes are provided with adhesive backing. In one embodiment, these electrodes are applied to the anterior chest region, the lateral chest region, or the posterior chest region with one cathode placed at the cardiac apex and the other anode to the region of the right upper sternal cardiac border. Additional electrodes may be applied to the patient for monitoring. Recording is digital with up to at least 45 minutes of event storage being preferable. Events may be recorded by patient initiation via an activator or automatic creation when rhythm criteria are met.

The device includes several unique features. First, the entire concept of a device for ambulatory monitoring for suspected bradycardia or prolonged QT with simultaneous ability to provide external pacing, recording and transmitting capability is unknown in conventional medicine.

Second, the device can include a leaf-shaped electrode with channels branching through its length and fenestrated, with one contact surface of the external channel being the patient's skin. A proximal end of the leaf can include a conducting media inject port, which allows refill of conducting media and dispersion across a large surface area of electrode-to-skin contact.

Third, the device can include a real-time impedance scanner/monitor with alert for delivering intermediate, periodic low voltage electrical output that is imperceptible to the patient. Impedance is measured and monitored. If impedance outside of a defined range occurs, alert (e.g., audio beeps) prompt refilling of the leaf-shaped electrode or physician representative attention to a lead or its contact. The latter may use Bluetooth technology to alert the physician to the increase in impedance.

Fourth, in one embodiment, the entire device may be composed of skin adhesive electrodes and pads that are adhered to the anterior, posterior, and/or lateral chest wall, thus minimizing the need for connecting cables. A belt or harness can be used to keep the device in position. The device has a pulse generator and an analyzer unit, a capacitor, a rechargeable battery, and an impedance monitor. The device also has the ability to use Bluetooth technology to communicate any sensed dysrhythmia or rise in impedance to the physician in real time, which safeguards against inappropriate pacing.

Finally, in another embodiment, the device's design is flatter, curvilinear in form so as to be capable of fitting within garments such as jackets, sweaters or belts. The device can also appear as and function as a belt buckle. In these embodiments, connection cables from the device to electrodes would be required.

Accordingly, the invention features an external cardiac pacing and monitoring device for monitoring and providing pacing to a patient's heart. The device includes a wearable impedance monitor for monitoring the patient's heart to detect bradycardia or prolonged QT interval, and at least two electrodes, which include an anode and a cathode that are removably attachable to a chest region of the patient and that are communicatively connected to the monitor. The monitor includes an electrical current generating device that is capable of providing external pacing to the patient via delivery of an electrical current from the monitor to the patient through the at least two electrodes when bradycardia or prolonged QT interval are detected.

In another aspect, the invention can feature the monitor further including a wireless transmitter for transmitting data to a remote computing device, wherein the data can include heart rate data, heart electrical cycle data, pulse, any reduction in conductive contact, and any data pertaining to any other physiological parameters of the patient capable of being detected via the at least two electrodes attached to the patient's chest region.

In another aspect, the invention can feature the wireless transmitter including Bluetooth technology for wireless transmission of the data to the remote computing device.

In another aspect, the invention can feature the remote computing device being a computer, a tablet computer, a cellular telephone, or any other suitable computing device.

In another aspect, the invention can feature the at least two electrodes being a single unitary electrode apparatus that is attachable to the patient's body.

In another aspect, the invention can feature the electrode apparatus having a generally leaf-like shape.

In another aspect, the invention can feature the electrode apparatus including fenestrations.

In another aspect, the invention can feature the electrode apparatus including a main channel and at least one side channel that is connected to the main channel.

In another aspect, the invention can feature the electrode apparatus further including an inject port through which conducting media is introduced into the electrode apparatus.

In another aspect, the invention can feature the monitor further including a memory component that stores data detected by the monitor and at least two electrodes, wherein the data is transmittable to a computing device.

In another aspect, the invention can feature the monitor being flexible so as to be capable of bending as the patient moves and changes position.

In another aspect, the invention can feature the monitor being connected internally or externally to a garment.

In another aspect, the invention can feature the monitor including a belt.

In another aspect, the invention can feature the monitor including a belt buckle.

In another aspect, the invention can feature the monitor further including an alert device that detects any reduction in conductive contact between the patient's body and the at least two electrodes and produces an audible alert, a visual alert, or both to alert the patient that conductive contact is reduced so that the patient may seek a refill of conducting media that is introduced into the at least two electrodes or reattachment of the at least two electrodes.

In another aspect, the invention can feature the monitor further including a wireless transmitter to transmit an alert signal signifying the reduction in conductive contact between the patient's body and the at least two electrodes to a remote receiver device, wherein the remote receiver device includes a receiver alert device that produces a remote audible alert, a remote visual alert, or both to alert a person monitoring the remote receiver device that conductive contact is reduced so that the patient may be provided with a refill of conducting media that is introduced into the at least two electrodes or with reattachment of the at least two electrodes to the patient's body when one or more of the at least two electrodes have become disconnected from the patient's body.

In another aspect, the invention can feature the monitor further including an alert device that produces an audible alert, a visual alert, or both to alert the patient that the monitor has detected bradycardia or prolonged QT interval so that the patient may seek medical attention.

The invention also features an external cardiac pacing and monitoring device that includes a wearable impedance monitor for monitoring a heart of a patient to detect bradycardia or prolonged QT interval and at least two electrodes, which include an anode and a cathode that are removably attachable to a chest region of the patient and that are communicatively connected to the monitor. The monitor includes an electrical current generating device that is capable of providing external pacing to the patient via delivery of an electrical current from the monitor to the patient through the at least two electrodes when bradycardia or prolonged QT interval are detected. The monitor further includes an alert device that detects any reduction in conductive contact between the patient's body and the at least two electrodes and produces an audible alert, a visual alert, or both to alert the patient that conductive contact is reduced. The monitor further includes a wireless transmitter to transmit an alert signal signifying the reduction in conductive contact between the patient's body and the at least two electrodes to a remote receiver device, wherein the remote receiver device comprises a receiver alert device that produces a remote audible alert, a remote visual alert, or both to alert a person monitoring the remote receiver device that conductive contact is reduced so that the patient may be provided with a refill of conducting media that is introduced into the at least two electrodes or with reattachment of the at least two electrodes to the patient's body when one or more of the at least two electrodes have become disconnected from the patient's body.

A method of the invention can be used for providing external cardiac pacing and monitoring to a patient. The method can include the step of: (a) removably attaching an external cardiac pacing and monitoring device to a chest region of a patient. The external cardiac pacing and monitoring device of the method can include a wearable impedance monitor for monitoring the patient's heart to detect bradycardia or prolonged QT interval, and at least two electrodes that can include an anode and a cathode that are removably attachable to the patient's chest region and that are communicatively connected to the monitor. The monitor is capable of providing external pacing to the patient via delivery of an electrical current from the monitor to the patient through the at least two electrodes. The method can further include the steps of: (b) monitoring the patient's heart rate, heart electrical cycle, pulse, and any other desired physiological parameters of the patient capable of being detected by the at least two electrodes; (c) detecting by the monitor of a condition, wherein the condition is selected from among one or more of the following conditions: (i) bradycardia, (ii) prolonged QT interval, and (iii) a reduction in conductive contact between the at least two electrodes and the patient's chest region; and (d) providing pacing to the patient's heart by delivering an electrical current from the monitor to the patient's heart via the at least two electrodes removably attached to the patient's chest region in response to the detection of any bradycardia or prolonged QT interval.

Another method of the invention can include the step of: (e) producing an audible alert, a visual alert, or both by an alert device to alert the patient to the presence of one or more of the conditions as detected by the monitor, wherein the monitor further includes the alert device as a component thereof.

Another method of the invention can include the step of: (f) transmitting wirelessly to a remote receiver device an alert signal signifying the presence of one or more of the conditions as detected by the monitor, wherein the remote receiver device can include a receiver alert device that produces a remote audible alert, a remote visual alert, or both to alert a person monitoring the remote receiver device.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents and other references mentioned herein are incorporated by reference in their entirety. In the case of conflict, the present specification, including definitions will control.

DETAILED DESCRIPTION

Figure 1A:
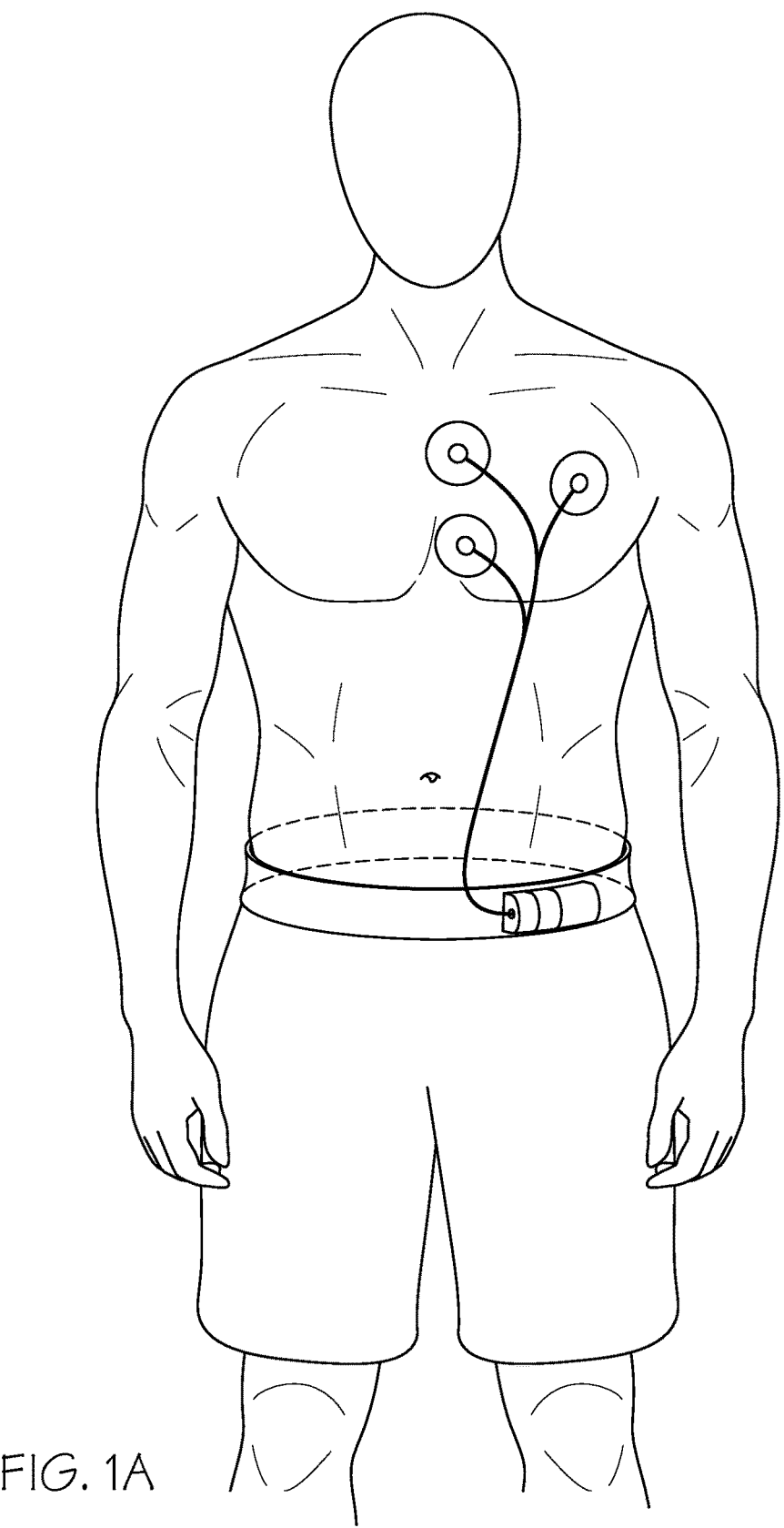
FIG. 1A shows one embodiment of a temporary external pacemaker and monitor.

The present invention is best understood by reference to the detailed drawings and description set forth herein. Embodiments of the invention are discussed below with reference to the drawings; however, those skilled in the art will readily appreciate that the detailed description given herein with respect to these figures is for explanatory purposes as the invention extends beyond these limited embodiments. For example, in light of the teachings of the present invention, those skilled in the art will recognize a multiplicity of alternate and suitable approaches, depending upon the needs of the particular application, to implement the functionality of any given detail described herein beyond the particular implementation choices in the following embodiments described and shown. That is, numerous modifications and variations of the invention may exist that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The present invention should not be limited to the particular methodology, compounds, materials, manufacturing techniques, uses, and applications, described herein, as these may vary. The terminology used herein is used for the purpose of describing particular embodiments only, and is not intended to limit the scope of the present invention. As used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" may be a reference to one or more steps or means and may include sub-steps and subservient means.

All conjunctions used herein are to be understood in the most inclusive sense possible. Thus, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise. Structures described herein are to be understood also to refer to functional equivalents of such structures. Language that may be construed to express approximation should be so understood unless the context clearly dictates otherwise.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "having" should be interpreted as "having at least"; the term "includes" should be interpreted as "includes but is not limited to"; the term "example" is used to provide exemplary instances of the item in discussion, not an exhaustive or limiting list thereof; and use of terms like "preferably," "preferred," "desired," "desirable," or "exemplary" and words of similar meaning should not be understood as implying that certain features are critical, essential, or even important to the structure or function of the invention, but instead as merely intended to highlight alternative or additional features that may or may not be utilized in a particular embodiment of the invention.

Those skilled in the art will also understand that if a specific number of an introduced claim recitation is intended, such an intent will be explicitly recited in the claim, and in the absence of such recitation no such intent is present. For example, as an aid to understanding, the appended claims may contain usage of the introductory phrases "at least one" and "one or more" to introduce claim recitations; however, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C" is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

All numbers expressing dimensions, quantities of ingredients, reaction conditions, and so forth used in the specification are to be understood as being modified in all instances by the term "about" unless expressly stated otherwise. Accordingly, unless indicated to the contrary, the numerical parameters set forth herein are approximations that may vary depending upon the desired properties sought to be obtained.

The invention provides an external cardiac pacing and monitoring device for ambulatory monitoring of a patient for suspected bradycardia or prolonged QT with simultaneous external pacing capability. If the patient has a significant bradycardic episode, the device will detect and record the episode during normal monitoring and will provide therapy. Likewise, if the QT suddenly prolongs or prolongs during monitoring, the device would provide pacing to shorten the QT and decrease the risk of torsade similar to defibrillation. This therapy allows the patient time to present himself to a physician or healthcare facility without suffering the results of temporary hemodynamic instability that might otherwise be associated with dysrhythmia after the dysrhythmia occurs. If the event was a bradyarrhythmia, a permanent pacemaker may be offered to the patient based on the documented bradycardia in cases in which the patient is otherwise stable. In this way, the device can act as a bridge between the time of diagnosis and the time of provision of more definitive therapy for patients with bradycardia. The device may also be used for initiation or escalation of outpatient antiarrhythmic therapy that might be otherwise associated with torsade from prolongation of the QT. The device can detect the change in QT interval from baseline, and based on an algorithm, apply pacing to shorten the QT and decrease the likelihood of torsade. This device is particularly useful for three situations: (1) monitoring for the purpose of diagnosing an arrhythmic etiology of symptoms of near syncope or syncope; (2) bradycardia prevention during the outpatient initiation of certain drugs with significant negative chronotropic potential; and (3) monitoring the QT interval in the latter patient subgroup for purposes of delivering overdrive suppression pacing to those with prolongation of the QT interval and the constant risk of torsade de pointes.

Figure 1B:
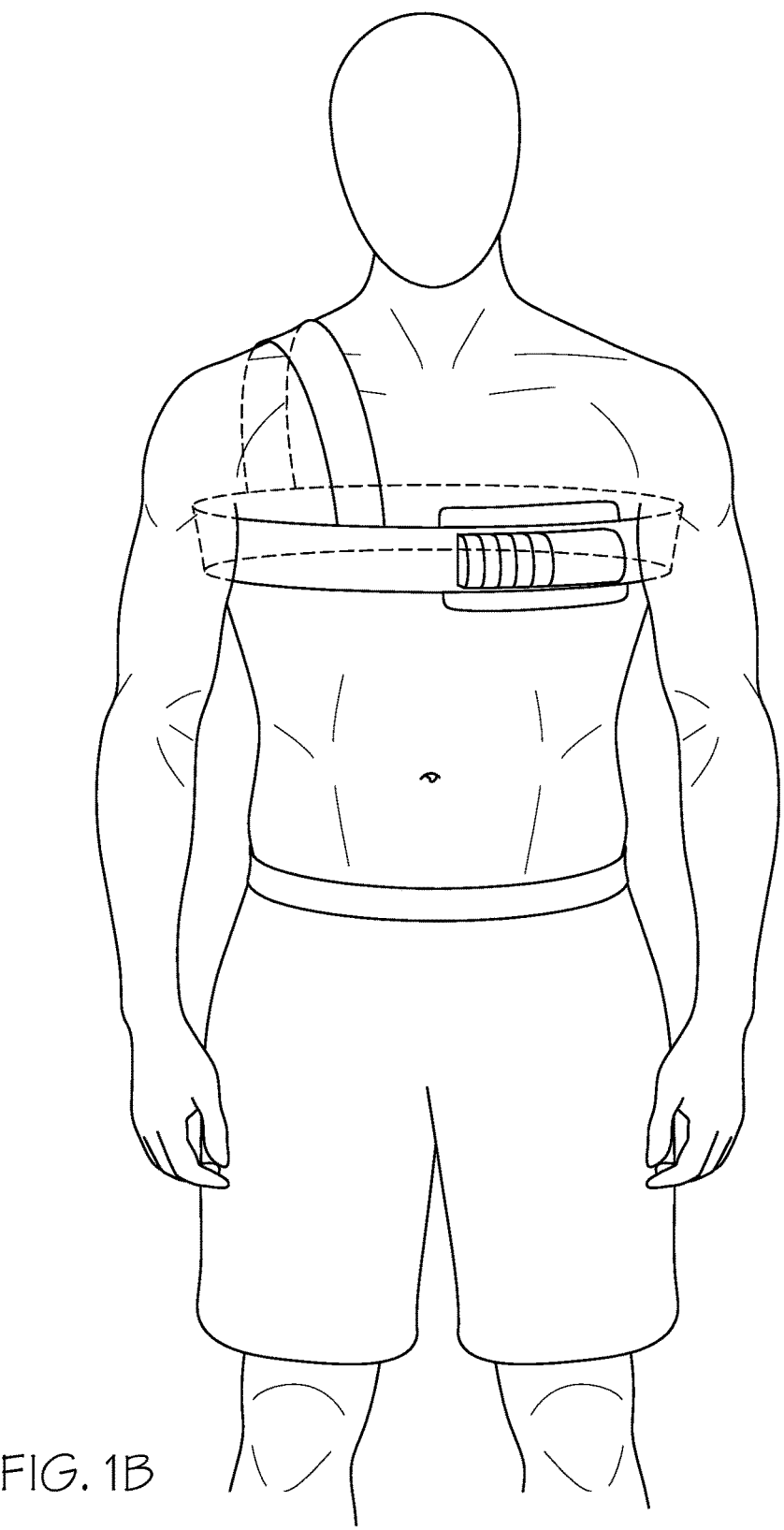
FIG. 1B shows another embodiment of a temporary external pacemaker and monitor.

Specifically, the device provides an impedance monitor having sensing, pacing, recording, and transmitting capabilities. FIGS. 1A and 1B illustrate two embodiments of the device. To provide pacing to the patient's heart, the monitor includes an electrical current generating device. Pacing can be provided on an as-needed basis based on the heart rate and heart electrical cycle data detected by the monitor via at least two electrodes (i.e., at least one anode and at least one cathode) that are removably attached to the patient's body at the chest region and that are communicatively connected to the monitor via wires. Future technology may permit wireless embodiments of the electrodes that transmit the patient's heart-related physiological data wirelessly to the monitor.

The pacing current delivery of the monitor's electrical current generating device involves transcutaneous electrical pacing using pulse durations of about 40, or alternatively, about 20 millisecond pulses with the capability of delivering up to about 140 to about 200 milliamps. The average current should be about 50 to about 100 milliamps with a range of about 60 to about 100 milliamps being required for unstable bradycardia and a range of about 50 to about 70 milliamps for hemodynamically stable patients. Pulse duration refers to the time of impulse stimulation. Using a longer pulse duration and larger electrodes permits the patients to tolerate higher applied current. The exact energy will be a programmable feature of the device based on the ability to offer consistent capture to assist a specific patient with minimal discomfort. The device uses a battery as a power source. In a preferred embodiment, the battery can be a rechargeable lithium battery with a low battery indicator light and an audio component for emitting periodic beep tones to alert the patient or other person concerning the battery reaching a critically low battery level. In an exemplary embodiment, the device can also include a second battery for use while the first battery is recharging.

The at least two electrodes can include two pacing electrodes that are provided with adhesive backing. In one embodiment, these electrodes (i.e., an anode and a cathode) can be applied to an anterior chest region of the patient with the cathode being removably attached to a region of the patient's chest region proximal to the patient's cardiac apex and the anode being removably attached to a region of the patient's chest proximal to the right upper sternal cardiac border. In other embodiments, the electrodes may be removably attached to other locations on the patient's body including, for example, to the lateral or posterior thorax. The electrodes can be about 20 cm$^2$ although electrodes of various other sizes both smaller and larger than the foregoing may be used. In an exemplary embodiment, the electrodes can be changed periodically. The electrodes used can be chosen for a balance between patient comfort in wearing electrodes, minimal surface area for effective ventricular capture at reasonable pacing outputs, and minimization of pain that may be associated with transcutaneous pacing. Pain sensation is minimized by using electrodes with surface areas of at least about 5 cm$^2$. The amount of pain for a current of a given strength reaches a plateau once the electrode surface exceeds about 10 cm$^2$.

Figure 2:
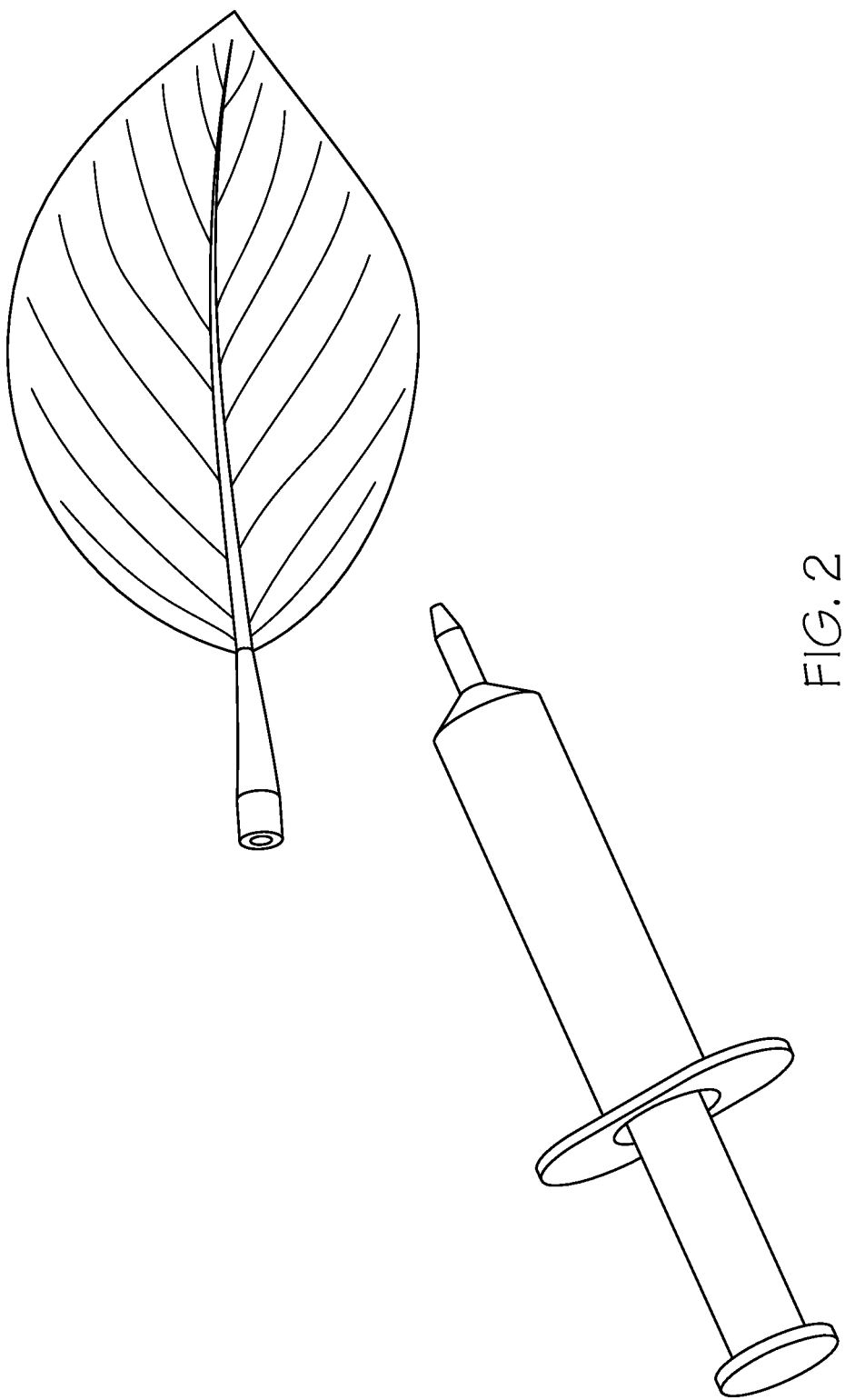
FIG. 2 shows an electrode that can be used with various embodiments of the temporary external pacemaker and monitor.

A suitable electrode apparatus, which includes at least two electrodes (i.e., at least one anode and at least one cathode), for use with the present invention is shown in FIG. 2. The electrode apparatus can be generally leaf-shaped (also referred to as generally ovate in shape as shown in FIG. 2) with a plurality of channels branching through its length and is fenestrated. In one embodiment, the leaf-shaped electrode apparatus may include, similar to a tree leaf, a longitudinal central channel with multiple side channels that connect to the central channel. One contact surface of the channels of the leaf-shaped electrode apparatus is the patient's skin. The proximal end of the electrode apparatus is provided with a conductive media inject port that allows refilling of the conductive media and dispersion across a large surface area of electrode skin contact. The general leaf shape of the electrode apparatus provides optimal and maximum coverage and contact of the patient's chest region proximal to the patient's cardiac apex and the region of the patient's chest proximal to the right upper sternal cardiac border so as allow for optimal monitoring and pacing of the patient's heart. Other embodiments of the electrodes may have difference shapes, sizes, and attachment means and configurations.

Determination of the electrode capture and pulse generation can be difficult when the skeletal muscle is stimulated due to considerable electrical artifact. As a result, in order to be able to provide useful recording of EKG data during periods of pacing, one of two methods should be employed. The first method involves blanking protection, which changes the high output pacing stimulus to a smaller EKG waveform. The second method involves the use of separate monitoring electrodes. In preferred embodiments of the invention, the second method is employed and separate monitoring electrodes are used. Thus, additional electrodes must be applied to the patient for monitoring; however, blanking protection as in the first method may used as an alternative.

The impedance monitor may also include a real-time impedance scanner with an alert device, which measures and monitors impedance as intermittent, periodic low frequency electrical output is delivered. The alert device may produce an audible alert, a visual alert, or both in response to one or more conditions that become present as detected by the monitor and the at least two electrodes removably attached to the patient. For example, if the impedance measured by the impedance scanner of the device is outside of a predetermined range, the alert device can produce an audio alert (e.g., a beep or other audible tone) prompting refill of the electrode or physician attention to the lead or its content. The device may include Bluetooth technology that allows communication between the impedance scanner and an audio alert device in the possession of or in proximity to the physician or other healthcare provider. In another embodiment, the alert device may include a visual alert. In still another embodiment, the alert device may include both visual and audible alerts.

When the monitor detects one or more of the conditions, which can include bradycardia, prolonged QT interval, changes in other monitored physiological parameters of the patient, or any reduction in conductive contact between the patient's body and the at least two electrodes, the alert device of the monitor can produce an audible alert, a visual alert, or both to alert the patient to the presence of the condition so that the patient can seek medical attention if necessary. For example, if the alert is triggered because conductive contact is reduced because the electrode apparatus requires a refill of conductive media, the patient may seek a refill of conducting media that is introduced into the at least two electrodes. In another example, if the alert is triggered as a result of conductive contact being reduced because one or more of the at least two electrodes has become partially or entirely detached from the patient's body, the patient may reattach the detached electrode or electrodes or seek assistance from a healthcare provider or other person with reattachment of the detached electrode or electrodes.

The alert produced by the alert device may vary by the condition that is detected by the monitor. In some embodiments, the alert device may produce a different alert in response to each type of condition that is detected by the monitor. For example, the color of a visual alert or the tone or sound of an audible alert may differ depending on the type of condition that is detected by the monitor. In other embodiments, the alert device may be programmed to produce only audible alerts when certain conditions are detected and only visual alerts when other different conditions are detected by the monitor. The alert device may also be programmed to produce various combinations of audible and/or visual alerts in response to the detection of certain conditions by the monitor. The time interval that the alert is produced by the alert device can be programmed to terminate after a predetermined time period, only after the condition that prompted the alert is no longer detected by the monitor, or after the alert device of the monitor is reset and the alert terminated manually, by wired electronic means, or by remote wireless means by the patient or by another person such as, for example, a physician, nurse, or other healthcare provider. In other embodiments, the alert device may produce the same alert or alerts regardless of the condition that is detected by the monitor.

In one embodiment, the monitor also can include a wireless transmitter to transmit an alert signal signifying one or more of the conditions to a remote receiver device. The remote receiver device includes a receiver alert device that produces a remote alert to alert a person monitoring the remote receiver device that conductive contact is reduced so that the patient may be provided with a refill of conducting media that is introduced into the at least two electrodes or with reattachment of the at least two electrodes to the patient's body when one or more of the at least two electrodes have become disconnected from the patient's body. The remote alert can be a remote audible alert, a remote visual alert, or both. The remote receiver device can be a computing device selected from those devices described elsewhere herein, a beeper, or any other suitable device capable of receiving the alert signal. The wireless transmitter can transmit the alert signal directly to the remote receiver device if the remote receiver device is within wireless range and is capable of receiving a wirelessly transmitted alert signal. In other embodiments, the monitor's wireless transmitter can include technology that communicatively connects the wireless transmitter to a communications network (e.g., the Internet, a local area network, or wide area network) via WiFi, Bluetooth, radio, cellular signal, or other wireless transmission protocols, methods, and means. A wireless router is necessary in embodiments that involve transmission of the alert signal wirelessly initially via WiFi to the Internet, which then transmits the signal to the intended remote receiver device.

The remote alert may vary by condition detected and transmitted to the remote receiver device by the monitor's wireless transmitted in ways similar to those described above with respect to the alerts that can be produced by the monitor's alert device. In some embodiments, the receiver alert device may produce a different alert in response to each type of condition that is detected by the monitor and transmitted to the remote receiver device. For example, the color of a visual alert or the tone or sound of an audible alert may differ depending on the type of condition that is detected by the monitor and transmitted to the remote receiver device. In other embodiments, the receiver alert device may be programmed to produce only audible alerts when certain conditions are detected and only visual alerts when other different conditions are detected and transmitted by the monitor. The receiver alert device may also be programmed to produce various combinations of audible and/or visual alerts in response to the detection of certain conditions for which alert signals are transmitted by the monitor. The time interval that the alert is produced by the receiver alert device can be programmed to terminate after a predetermined time period, only after the condition that prompted the alert is no longer detected by the monitor so that transmission of the alert signal that prompted the remote alert has ceased, or after the receiver alert device is reset and the remote alert terminated manually, by wired electronic means, or by remote wireless means by the person monitoring the remote receiver device such as, for example, a physician, nurse, or other healthcare provider. In other embodiments, the receiver alert device may produce the same alert or alerts regardless of the condition that is detected and transmitted by the monitor.

The monitor of the device may be manufactured in different shapes and sizes and may be constructed for wearing externally on a belt clip or to fit within a belt or other garment such as a shirt, sweater, or pants. In one alternate embodiment, the device can include a monitor that is approximately the same size and shape as a belt buckle. In that embodiment, the monitor may also function as a belt buckle. By incorporating the monitor of the device into a garment, belt, or belt buckle, the monitor can be concealed so that it is not visible or at least not readily identifiable by other persons when worn by the patient. The pacing leads can be patch electrodes with connecting wire; however, if the device is placed directly on the sternum, the need for connecting wires is minimized.

The device can record digitally at a sampling frequency of kilohertz preferably in a continuous loop fashion. Up to about 45 minutes of event storage is preferred. Other embodiments may include more or less event storage. Events are recorded by either patient initiation via an activator connected to the device, or by automatic creation of event records when rhythm criteria are met or in the setting of QT monitoring when QT interval change reaches a predetermined threshold. The duration of event storage pre- and post-automatic detection criteria are programmable features as are transmission in real time to medical personnel or trained monitoring personnel. If a bradycardic event is detected by the monitor, the device paces the patient through the electrodes. This pacing gives the patient a greater chance of remaining conscious during the dysrhythmia. The pacing acts to provide the patient with an opportunity to present him or herself to a physician, emergency room, urgent care center, or other healthcare provider or facility for care, preferably without suffering syncope and possible trauma. The transmission of the dysrhythmia by the device allows the physician to determine if pacing is justified and to communicate with the patient to allow the device to be removed if pacing is not justified.

The monitor can include a memory device capable of storing data detected by the at least two electrodes and transmitted to the monitor. The monitor can also include a processor or other electrical or electronic hardware and software that commences pacing by transmission of electrical current from the monitor to the patient's heart via the at least two electrodes when bradycardia or prolonged QT interval are detected. In one embodiment, the monitor is programmable to provide pacing for a predetermined or programmed interval of time. In another embodiment, the monitor can provide pacing until bradycardia, prolonged QT interval, or other monitored physiological parameters are no longer present in the patient's condition. In still another embodiment, the monitor can provide pacing until the monitor is reset and pacing terminated by a healthcare provider either by manual, wired electronic, or remote wireless means.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An external cardiac pacing and monitoring device comprising:
   a wearable impedance monitor for measuring an impedance and for monitoring a patient to detect bradycardia or prolonged QT interval; and
   a single unitary electrode apparatus that is removably attachable to a chest region of the patient, wherein the electrode apparatus comprises at least two electrodes comprising an anode and a cathode that are communicatively connected to the monitor; and wherein the electrode apparatus comprises a generally ovate leaf shape to provide optimal and maximum coverage and contact of the patient's chest region proximal to the patient's cardiac apex and the region of the patient's chest proximal to the patient's right upper sternal cardiac border, and branching channels and fenestrations for a conducting media;
   wherein the monitor further comprises an electrical current generating device that is capable of providing external pacing to the patient via delivery of an electrical current from the monitor to the patient through the at least two electrodes when bradycardia or prolonged QT interval are detected.

2. The device of claim 1, wherein the monitor further detects heart rate data and heart electrical cycle data;

wherein the monitor further comprises a wireless transmitter for transmitting data to a remote computing device; and wherein the data comprises the heart rate data and heart electrical cycle data obtained from the patient via the at least two electrodes attached to the patient's chest region and detected by the monitor.

3. The device of claim 2, wherein the wireless transmitter comprises Bluetooth technology for wireless transmission of the data to the remote computing device.

4. The device of claim 2, further comprising the remote computing device, wherein the remote computing device comprises a computer, a tablet computer, a cellular telephone, or any other suitable computing device.

5. The device of claim 1, wherein the branching channels and fenestrations comprise a main channel and at least one side channel that is connected to the main channel.

6. The device of claim 1, wherein the electrode apparatus further comprises an inject port through which the conducting media is introduced into the electrode apparatus.

7. The device of claim 1, wherein the monitor further detects heart rate data and heart electrical cycle data; wherein the monitor further comprises a memory component that stores the heart rate data and heart electrical cycle data detected by the monitor and at least two electrodes; and wherein the heart rate data and heart electrical cycle data are transmittable to a computing device.

8. The device of claim 1, wherein the monitor is flexible so as to be capable of bending as the patient moves and changes position.

9. The device of claim 1, further comprising a garment, wherein the monitor is connected internally or externally to the garment.

10. The device of claim 1, wherein the monitor is part of a belt.

11. The device of claim 1, wherein the monitor is part of a belt buckle.

12. The device of claim 1, wherein the monitor further comprises an alert device that is configured to detect any reduction in conductive contact between the patient's body and the at least two electrodes and produces an audible alert, a visual alert, or both to alert the patient that conductive contact is reduced so that the patient may seek a refill of conducting media that is introduced into the at least two electrodes or reattachment of the at least two electrodes.

13. The device of claim 12, further comprising a remote receiver device; wherein the monitor further comprises a wireless transmitter to transmit an alert signal signifying the reduction in conductive contact between the patient's body and the at least two electrodes to the remote receiver device; and wherein the remote receiver device comprises a receiver alert device that produces a remote audible alert, a remote visual alert, or both to alert a person monitoring the remote receiver device that conductive contact is reduced so that the patient may be provided with a refill of conducting media that is introduced into the at least two electrodes or with reattachment of the at least two electrodes to the patient's body when one or more of the at least two electrodes have become disconnected from the patient's body.

14. The device of claim 1, wherein the monitor further comprises an alert device that produces an audible alert, a visual alert, or both to alert the patient that the monitor has detected bradycardia or prolonged QT interval so that the patient may seek medical attention.

15. An external cardiac pacing and monitoring device comprising:

a wearable impedance monitor for measuring an impedance and for monitoring a patient to detect bradycardia or prolonged QT interval; and
a single unitary electrode apparatus that is removably attachable to a chest region of the patient, wherein the electrode apparatus comprises at least two electrodes comprising an anode and a cathode that are communicatively connected to the monitor, wherein the electrode apparatus comprises a generally ovate leaf shape to provide optimal and maximum coverage and contact of the patient's chest region proximal to the patient's cardiac apex and the region of the patient's chest proximal to the patient's right upper sternal cardiac border, and branching channels and fenestrations for a conducting media; and
a remote receiver device;
wherein the monitor further comprises an electrical current generating device that is capable of providing external pacing to the patient via delivery of an electrical current from the monitor to the patient through the at least two electrodes when bradycardia or prolonged QT interval are detected;
wherein the monitor further comprises an alert device that is configured to detect any reduction in conductive contact between the patient's body and the at least two electrodes and produces an audible alert, a visual alert, or both to alert the patient that conductive contact is reduced;
wherein the monitor further comprises a wireless transmitter to transmit an alert signal signifying the reduction in conductive contact between the patient's body and the at least two electrodes to the remote receiver device; and
wherein the remote receiver device comprises a receiver alert device that produces a remote audible alert, a remote visual alert, or both to alert a person monitoring the remote receiver device that conductive contact is reduced so that the patient may be provided with a refill of conducting media that is introduced into the at least two electrodes or with reattachment of the at least two electrodes to the patient's body when one or more of the at least two electrodes have become disconnected from the patient's body.

16. A method for providing external cardiac pacing and monitoring to a patient, the method comprising the steps of:
(a) removably attaching an external cardiac pacing and monitoring device to a chest region of a patient, wherein the external cardiac pacing and monitoring device comprises:
a wearable impedance monitor for measuring an impedance and for monitoring a patient to detect bradycardia or prolonged QT interval; and
a single unitary electrode apparatus that is removably attachable to a chest region of the patient, wherein the electrode apparatus comprises at least two electrodes comprising an anode and a cathode that are communicatively connected to the monitor, wherein the electrode apparatus comprises a generally ovate leaf shape to provide optimal and maximum coverage and contact of the patient's chest region proximal to the patient's cardiac apex and the region of the patient's chest proximal to the patient's right upper sternal cardiac border, and branching channels and fenestrations for a conducting media;
wherein the monitor is further capable of providing external pacing to the patient via delivery of an electrical current from the monitor to the patient through the at least two electrodes;

(b) monitoring the patient's heart rate, heart electrical cycle, and pulse using the monitor;

(c) detecting by the monitor a condition, wherein the condition comprises at least one condition selected from the group consisting of: (i) bradycardia, (ii) prolonged QT interval, and (iii) a reduction in conductive contact between the at least two electrodes and the patient's chest region; and (d) when bradycardia or prolonged QT interval are detected by the monitor, providing pacing to the patient's heart by delivering an electrical current from the monitor to the patient's heart via the at least two electrodes removably attached to the patient's chest region in response to the detection of any bradycardia or prolonged QT interval.

17. The method of claim 16, further comprising at least one of the following steps:

(e) producing an audible alert, a visual alert, or both by an alert device to alert the patient to the presence of one or more of the conditions as detected by the monitor, wherein the monitor comprises the alert device as a component thereof; and (f) transmitting wirelessly to a remote receiver device an alert signal signifying the presence of one or more of the conditions as detected by the monitor, wherein the remote receiver device comprises a receiver alert device that produces a remote audible alert, a remote visual alert, or both to alert a person monitoring the remote receiver device.

* * * * *